United States Patent
Ternes et al.

(10) Patent No.: US 7,177,689 B2
(45) Date of Patent: Feb. 13, 2007

(54) METHOD AND APPARATUS FOR CAPTURE VERIFICATION AND THRESHOLD DETERMINATION

(75) Inventors: David Ternes, Roseville, MN (US); David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 169 days.

(21) Appl. No.: 10/003,718

(22) Filed: Oct. 26, 2001

(65) Prior Publication Data

US 2003/0083710 A1    May 1, 2003

(51) Int. Cl.
*A61N 1/365* (2006.01)

(52) U.S. Cl. ...................................... 607/28

(58) Field of Classification Search ............... 600/373, 600/374, 393, 509, 519; 607/4, 5, 7, 9, 11, 607/20, 30, 32, 119, 28; 128/903
See application file for complete search history.

(56) References Cited

U.S. PATENT DOCUMENTS

| | | | |
|---|---|---|---|
| 4,832,041 A | 5/1989 | Wang et al. ................. 128/697 |
| 4,895,152 A * | 1/1990 | Callaghan et al. ............ 607/13 |
| 5,273,049 A | 12/1993 | Steinhaus et al. ........... 128/696 |
| 5,312,445 A | 5/1994 | Nappholz et al. .............. 607/9 |
| 5,330,511 A | 7/1994 | Boute |
| 5,331,966 A | 7/1994 | Bennett et al. ............. 128/696 |
| 5,334,220 A | 8/1994 | Sholder |
| 5,340,361 A | 8/1994 | Sholder |
| 5,350,410 A | 9/1994 | Kleks et al. |
| 5,391,192 A | 2/1995 | Lu et al. ....................... 607/28 |
| 5,458,623 A * | 10/1995 | Lu et al. ....................... 607/28 |
| 5,534,016 A | 7/1996 | Boute |
| 5,626,623 A | 5/1997 | Kieval et al. |
| 5,660,184 A | 8/1997 | Donehoo et al. ........... 128/696 |
| 5,674,254 A | 10/1997 | van Krieken ................ 607/11 |
| 5,741,308 A | 4/1998 | Sholder |
| 5,755,739 A | 5/1998 | Sun et al. ...................... 607/14 |
| 5,771,898 A | 6/1998 | Marinello ................... 128/697 |
| 5,778,881 A | 7/1998 | Sun et al. ................... 128/696 |
| 5,782,888 A | 7/1998 | Sun et al. ..................... 607/27 |
| 6,029,088 A | 2/2000 | Budgifvars et al. |
| 6,101,416 A | 8/2000 | Sloman ....................... 607/28 |
| 6,128,535 A | 10/2000 | Maarse |
| 6,169,921 B1 | 1/2001 | KenKnight et al. ............ 607/4 |
| 6,456,881 B1 | 9/2002 | Bornzin |
| 6,512,953 B2 * | 1/2003 | Florio et al. .................. 607/28 |

(Continued)

FOREIGN PATENT DOCUMENTS

EP    1123716    8/2001

(Continued)

*Primary Examiner*—Robert E. Pezzuto
*Assistant Examiner*—Frances P. Oropeza
(74) *Attorney, Agent, or Firm*—Schwegman, Lundberg, Woessner & Kluth

(57) ABSTRACT

An apparatus and method for verifying capture by a pacing pulse in which a test depolarization waveform recorded during a pacing event is compared with a template waveform representing capture by the pacing pulse. Capture verification in this manner may be used in pacemakers having multiple pacing channels for the atrial and/or ventricles where the multiple paces can interfere with conventional sensing of evoked responses in order to verify capture.

19 Claims, 5 Drawing Sheets

U.S. PATENT DOCUMENTS

| | | |
|---|---|---|
| 6,697,673 B1 | 2/2004 | Lu |
| 6,738,669 B1 | 5/2004 | Sloman et al. |
| 6,829,505 B2 | 12/2004 | Kramer et al. |
| 6,904,321 B1 * | 6/2005 | Bornzin et al. ............... 607/27 |
| 2001/0049542 A1 | 12/2001 | Florio et al. |
| 2001/0049543 A1 | 12/2001 | Kroll |
| 2003/0083711 A1 | 5/2003 | Yonce et al. |
| 2004/0158165 A1 | 8/2004 | Yonce et al. |
| 2004/0158293 A1 | 8/2004 | Yonce et al. |

FOREIGN PATENT DOCUMENTS

| | | |
|---|---|---|
| EP | 1155711 | 11/2001 |
| WO | WO-2004026398 A1 | 4/2004 |

* cited by examiner

METHOD AND APPARATUS FOR CAPTURE VERIFICATION AND THRESHOLD DETERMINATION

FIELD OF THE INVENTION

This invention pertains to cardiac pacemakers and, in particular, to systems and methods for ascertaining the performance of the device and adjusting pacing parameters accordingly.

BACKGROUND

Implantable cardiac pacemakers are a class of cardiac rhythm management devices that provide electrical stimulation in the form of pacing pulses to selected chambers of the heart. (As the term is used herein, a pacemaker is any cardiac rhythm management device with a pacing functionality regardless of any additional functions it may perform such as cardioversion/defibrillation.) Pacemakers typically have a programmable electronic controller that causes the pacing pulses to be output in response to lapsed time intervals and sensed electrical activity (i.e., intrinsic heart beats). Most pacemakers are programmed to operate in a so-called demand mode (a.k.a., synchronous mode), where a pacing pulse is delivered to a heart chamber during a cardiac cycle only when no intrinsic beat by the chamber is detected. An escape interval is defined for each paced chamber, which is the minimum time interval in which a beat must be detected before a pace will be delivered. The ventricular escape interval thus defines the minimum rate at which the pacemaker will allow the heart to beat, sometimes referred to as the lower rate limit. If functioning properly, the pacemaker in this manner makes up for a heart's inability to pace itself at an appropriate rhythm.

In order for a pacemaker to control the heart rate in the manner described above, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a demand pacemaker that is not achieving capture is not performing its function in enforcing a minimum heart rate. A number of factors can determine whether a given pacing pulse will achieve capture, but the principal factor of concern here is the energy of the pulse, which is a function of the pulse's amplitude and duration. The minimum pacing pulse energy necessary to achieve capture by a particular pacing channel is referred to as the capture threshold. Programmable pacemakers enable the amplitude and pulse width of pacing pulses to be adjusted, along with other parameters. It is common practice to determine the capture threshold by initially pacing with a high energy to ensure capture and then progressively lowering the pacing pulse energy during a sequence of cardiac cycles until capture is no longer achieved. The pacing pulse energy can then be adjusted to an appropriate value in accordance with the determined capture threshold by setting it equal to the capture threshold plus a specified safety margin.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting an evoked atrial or ventricular depolarization that exceeds a specified value (i.e., corresponding to an evoked P-wave or evoked R-wave, respectively, on a surface electrocardiogram or their equivalents in an internal electrogram), the pacemaker is able to detect whether the pacing pulse (A-pulse or V-pulse) was effective in capturing the heart, that is, causing a contraction in the respective heart chamber. Capture verification can be performed in the clinical setting, with the clinician then adjusting pacing parameters so that the heart is reliably paced. It is desirable, however, for the pacemaker itself to be capable of verifying capture so that loss of capture can be detected when it occurs with pacing parameters then adjusted automatically, a function known as autocapture. (See, e.g., U.S. Pat. No. 6,169,921 issued to KenKnight, et. al. and presently assigned to the Guidant Corp.) An autocapture function provides the pacemaker with extended longevity, greater ease of use, and greater patient safety.

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses in a manner that results in a coordinated contraction of both atria and both ventricles. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output. The resulting diminishment in cardiac output may be significant in a patient with congestive heart failure (CHF) whose cardiac output is already compromised. Intraventricular and/or interventricular conduction defects can also be a cause of CHF in some patients. In order to treat these problems, pacemakers have been developed which provide multi-site electrical pacing stimulation to one or both of the atria and/or ventricles during a cardiac cycle in an attempt to improve the coordination of atrial and/or ventricular contractions, termed cardiac resynchronization therapy. To optimize the cardiac output for some heart failure patients, for example, the right and left ventricles are paced synchronously with a determined time offset, termed biventricular pacing.

Multi-site resynchronization pacing, however, is problematic for conventional capture verification methods based upon evoked response detection as described above. In biventricular pacing, for example, the proximity in time of resynchronization paces to the left and right ventricles may prevent an evoked response caused by the first pace from being distinguished from the second pace. In addition, the second pace could interfere with evoked response sensing when the evoked response from the first pace occurs within an amplifier blanking interval initiated by the second pace.

SUMMARY OF THE INVENTION

A depolarization waveform, such as a surface electrocardiogram (ECG) or internal electrogram from by an implanted pacemaker, recorded during a paced event that achieves capture exhibits morphological differences from that recorded during a paced event that fails to achieve capture. Also, when multiple pacing pulses are delivered to either the atria or the ventricles during a cardiac cycle, the morphology of the depolarization waveform that results is affected if even one of the pacing pulses fails to achieve capture. In accordance with the invention, capture of the heart by a pacing pulse is determined by comparing a test depolarization waveform recorded during the paced event with a template waveform representing capture of the heart by a similarly delivered pacing pulse. The comparison may be done by cross-correlating the template and test waveforms so that loss of the capture is detected when the two waveforms become uncorrelated. In a multi-site pacing situation, template waveforms representing capture by each pace individually and by all of the paces collectively can be used determine which pace failed to achieve capture and to simplify the determination of capture thresholds for each pacing site.

DETAILED DESCRIPTION

Figure 1:
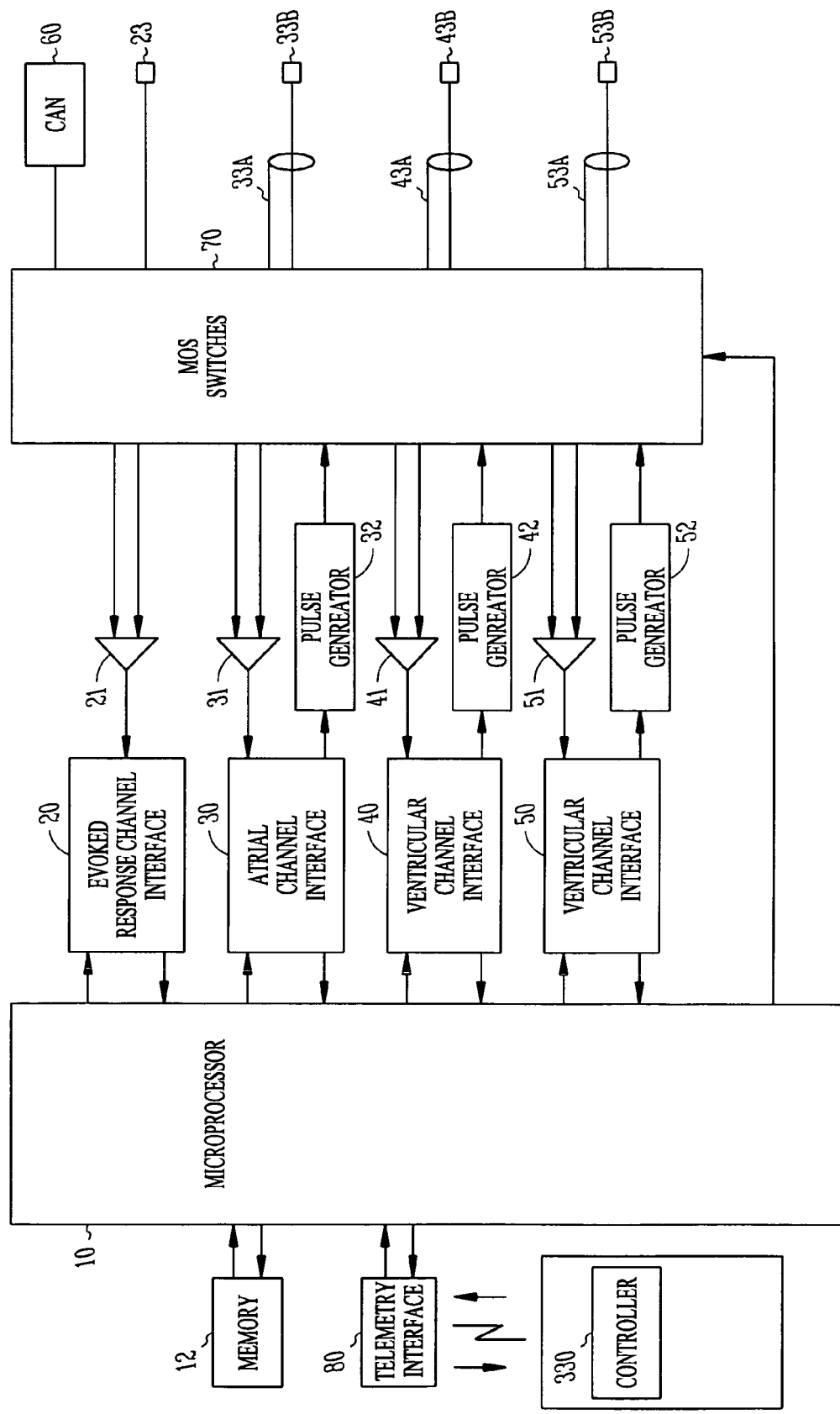
FIG. 1 is a block diagram of a multi-site pacemaker.

The present invention may be incorporated into pacemakers having a number of different pacing configurations, including multi-site pacing configurations for delivering various types of resynchronization therapy where a pace is delivered to each of the paired atria and/or ventricles during a cardiac cycle or where multiple paces are delivered to a single chamber. For illustrative purposes, however, the invention will be described with reference to a dual-chamber pacemaker (i.e., one that senses and/or paces both the atria and ventricles) having two ventricular pacing channels for pacing both ventricles or delivering two paces to a single ventricle as shown in FIG. 1.

a. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above the capture threshold must be delivered to the chamber.

The controller of the pacemaker is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with a controller 330 that can interrogate the pacemaker and receive stored data as well as adjust the operating parameters of the pacemaker.

The pacemaker has an atrial sensing/pacing channel comprising ring electrode 33$a$, tip electrode 33$b$, sense amplifier 31, pulse generator 32, and an atrial channel interface 30 which communicates bidirectionally with a port of microprocessor 10. The device also has two ventricular sensing/pacing channels that similarly include ring electrodes 43$a$ and 53$a$, tip electrodes 43$b$ and 53$b$, sense amplifiers 41 and 51, pulse generators 42 and 52, and ventricular channel interfaces 40 and 50. For each channel, the electrodes are connected to the pacemaker by a lead and used for both sensing and pacing. A MOS switching network 70 controlled by the microprocessor is used to switch the electrodes from the input of a sense amplifier to the output of a pulse generator. The pacemaker also has an evoked response sensing channel that comprises an evoked response channel interface 20 and a sense amplifier 21 that has its differential inputs connected to a unipolar electrode 23 and to the device housing or can 60 through the switching network 70. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 10 controls the overall operation of the device in accordance with programmed instructions stored in memory. The sensing circuitry of the pacemaker generates atrial and ventricular sense signals when voltages sensed by the electrodes exceed a specified threshold. The controller then interprets sense signals from the sensing channels and controls the delivery of paces in accordance with a programmed pacing mode. The sense signals from any of the sensing channels of the pacemaker in FIG. 1 can be digitized and recorded by the controller to constitute an electrogram that can either be transmitted via the telemetry link 80 to the external programmer 300 or stored for later transmission. The patient's cardiac activity may thus be observed in real-time or over a selected historical period.

In accordance with the invention, an electrogram can also be recorded of an evoked response to a pace and used to determine if capture is achieved by comparing the recorded electrogram with a template electrogram representing capture of the heart by a similarly delivered pace. An evoked response is the wave of depolarization that results from a pacing pulse and, since it evidences that the paced chamber has responded appropriately and contracted, it can be used to verify that the pace has achieved capture of the heart. An evoked response sensing channel for recording an electrogram can be a sensing channel normally used for other purposes or can be a sensing channel dedicated to sensing evoked responses. It is preferable to record the electrogram with a unipolar electrode that "sees" a larger volume of the myocardium as a wave of electrical activity spreads than a bipolar electrode. In the embodiment illustrated in FIG. 1, the atrial and ventricular sensing pacing channels utilize bipolar electrodes, and a dedicated evoked response sensing channel is provided with a unipolar electrode. Alternate embodiments may employ unipolar electrodes in the atrial and/or sensing/pacing channels, in which case unipolar sensing of an evoked response may be performed with those channels instead of a dedicated channel.

b. Capture Verification and Threshold Determination

In accordance with the invention, capture of heart by multiple pacing pulses delivered to the atria and/or ventricles during a cardiac cycle is determined by recording a test depolarization waveform during the paces and comparing the test waveform with a template depolarization waveform representing capture of the heart by at least one pacing pulse. Although the method described herein for capture verification and threshold determination may be applied to any multi-site pacing configuration, the following detailed explanation and description of specific embodiments will be confined to a biventricular pacing configuration where both ventricles are paced during a cardiac cycle separated by a programmed offset.

Figure 2A:
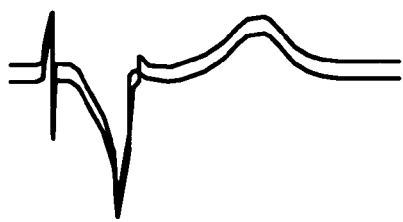
FIGS. 2A and 2B illustrate an ECG recorded after a pace and a template ECG.
Figure 2B:
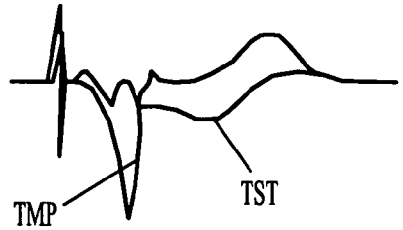

Delivery of multiple paces to the ventricles during a cardiac cycle changes the pattern of the resulting depolarization as compared with the pattern that results from a single ventricular pace. This difference appears as a QRS wave morphology change in a recorded depolarization waveform such as a surface ECG or electrogram that senses the time-varying net dipole vector produced by the depolarization. A reference morphology template waveform can be created by recording a ventricular ECG or electrogram during a biventricular pacing cycle that is known to achieve capture with both pacing pulses. Presence or absence of capture for a given pace can then be determined by comparing the template waveform with a test depolarization waveform recorded during the pace. FIG. 2A shows an example of a template ECG waveform TMP and a test ECG waveform TST that match, while FIG. 2B show test and template waveforms that are morphologically different because of a failure to achieve capture by one of the pacing pulses. The comparison may be accomplished, for example, by performing a time-domain cross-correlation between the template and test waveforms. Loss of capture at one of the ventricular pacing sites is then indicated by a loss of correlation between the test and template waveforms. The exact correlation values that should optimally be used in deciding whether or not a test waveform and template waveform match may be selected on the basis of empiric testing as the optimum values may vary for an individual patient and/or pacemaker. Capture verification performed in this manner may be used to determine the capture threshold of a pacing channel by varying the pacing pulse energy and finding the minimum energy that results in capture.

Capture verification and threshold determination as described above may be accomplished in a number of different ways. In one exemplary embodiment, a surface ECG is recorded with conventional leads during pacing by an external programmer that communicates with the implanted pacemaker via a radio telemetry link. The processor of the external programmer then performs the correlation between the test ECG and a template ECG to determine if capture is achieved by the pacing pulses. In a modification to this embodiment, rather than using surface ECGs, a test electrogram recorded by an evoked response sensing channel of the pacemaker and transmitted to the external programmer is compared with a template electrogram to verify capture. The external programmer can employ the telemetry link to adjust the pacing pulse energy in order to determine the capture threshold and then set the pacing pulse energy at an appropriate value, either under the direction of a clinician or automatically by software running in the external programmer.

In another embodiment, the controller of the pacemaker is programmed to verify capture by comparing the test electrogram with the template electrogram and to determine the capture threshold by varying the pacing pulse energy, either autonomously at selected times or in accordance with instructions received over the telemetry link. The controller may then be further programmed to automatically set the pacing pulse energy in accordance with the determined capture threshold. Determination of the capture threshold may be performed automatically on a periodic basis or at the direction of a clinician communicating with an external programmer. The controller may also be programmed to verify capture by pacing pulses on a beat-to-beat basis. If a loss of capture is detected, the controller can then perform a capture threshold determination and adjust the pacing pulse energy as appropriate. Loss of capture events may also be logged in the memory of the controller for later transmission to an external programmer.

Figure 3A:
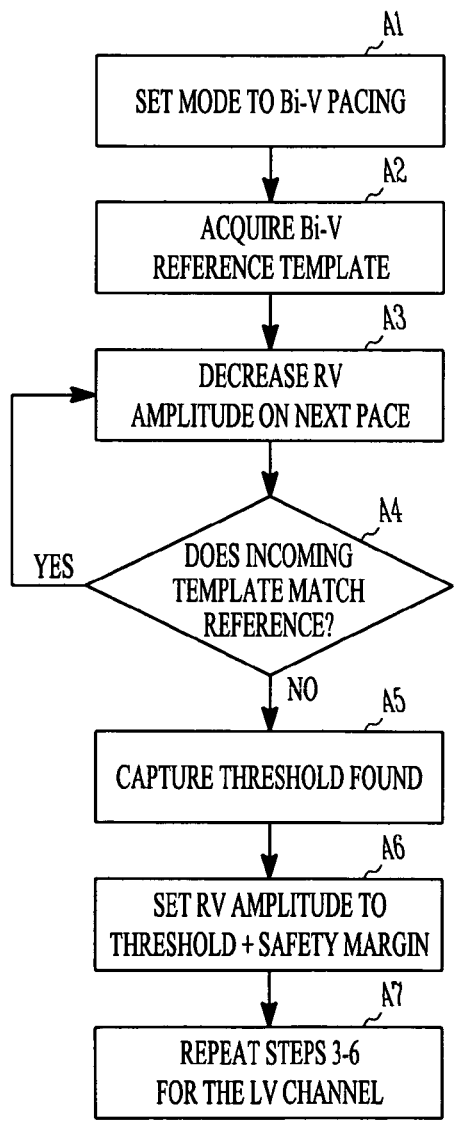
FIGS. 3A and 3B illustrate exemplary embodiments of algorithms for capture threshold determination.

FIG. 3A illustrates an exemplary procedure for determining the threshold voltage of the right and left ventricular pacing channels (referred to as RV and LV, respectively) in a bi-ventricular pacemaker using ECG or electrogram waveforms. The auto-threshold algorithm begins at steps A1 and A2 by pacing both chambers of the heart and recording an ECG or electrogram to create a biventricular (Bi-V) template waveform that is to be used as a reference. The pacing pulse amplitude for both ventricles is set at a relatively high value to ensure capture during acquisition of the biventricular template waveform. After the template waveform is obtained, the system decreases one of the pacing amplitudes at step A3, in this case the RV pacing amplitude, before the next pace. The RV pace triggers the recording of an incoming ECG or electrogram following the pace that is to be used as the test waveform in verifying capture. A cross correlation analysis is performed between the template waveform and the test waveform at step A4. If the waveforms correlate well, then both ventricular pacing channels are assumed to have achieved capture and step A3 is repeated to decrease the RV pacing amplitude. If loss of correlation is detected at step A4, then the RV pacing amplitude is assumed to have dropped below the threshold voltage. The capture threshold is then determined at step A5 to be the RV pacing amplitude before the decrease at step A3. The system then sets the RV pacing pulse amplitude to the threshold voltage plus some safety factor at step A6. Steps A3 through A6 are then repeated for the LV pacing channel as indicated by step A7 in order find the LV capture threshold and set the LV pacing amplitude.

In single-site pacing systems utilizing capture verification, it is desirable to quickly pace the heart once a loss of capture occurs. This becomes especially important with pacing-dependent patients in order to maintain cardiac activity. Often the delay associated with the external programmer ECG and with the telemetry systems used for communication between the external programmer and the pacemaker can prohibit immediate safety pacing. Note, however, that the bi-ventricular auto-threshold algorithm presented above inherently includes a safety back-up pace with the additional ventricular pacing channel. Once one channel loses capture, the other still causes contraction of the ventricles, maintaining ventricular function. Because of the safety provided by two ventricular pacing sites, the auto-threshold algorithm could also start with one output high and increase the other from a sub-threshold voltage. For example, a template can be created for RV-only pacing. The LV pacing amplitude then increases from a sub-threshold voltage until the system detects Bi-V pacing. This flexibility thus facilitates the use of more efficient search algorithms to speed convergence to the proper threshold value.

Figure 3B:
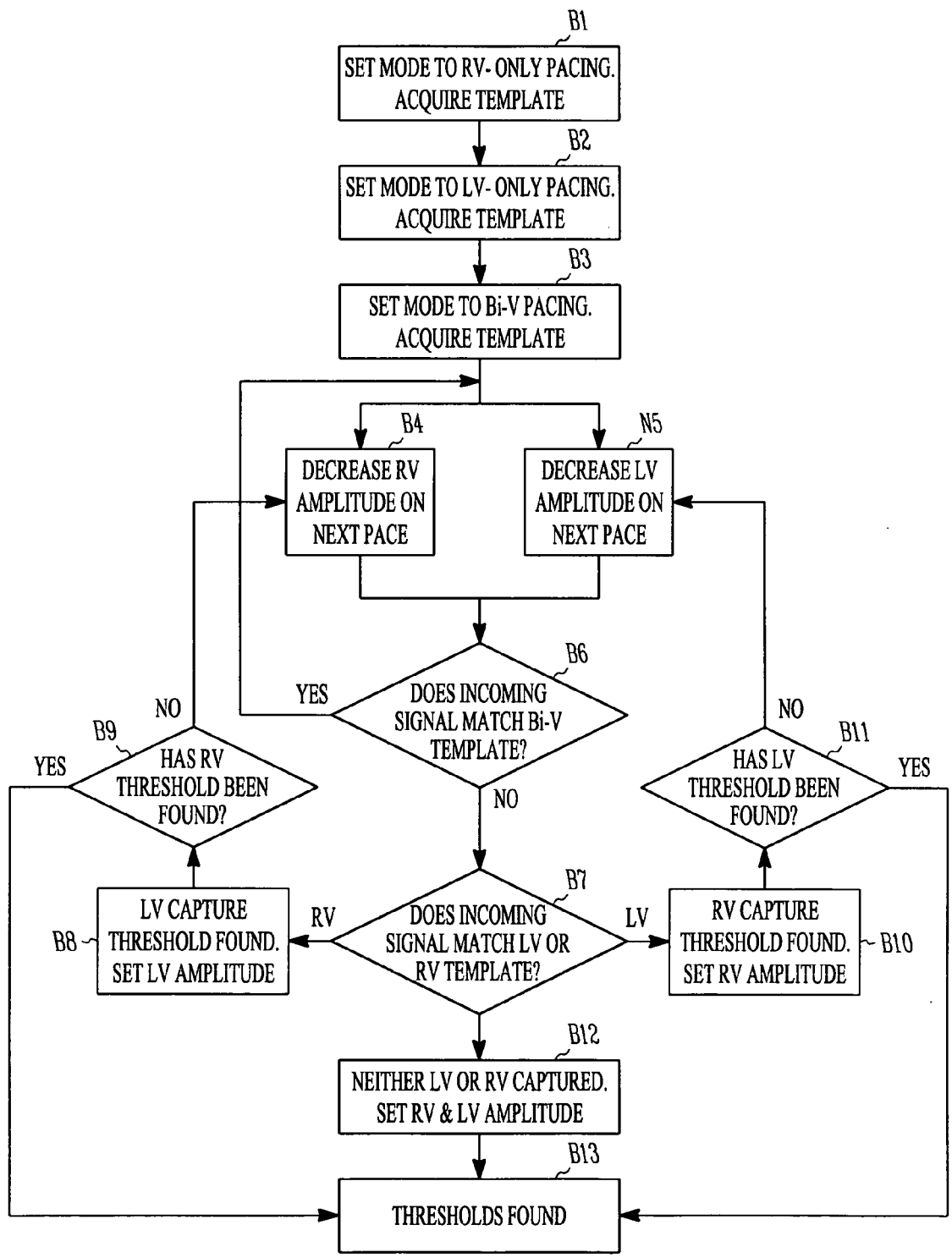

Another exemplary procedure is illustrated by FIG. 3B that decreases the total time of the auto-threshold algorithm by determining the LV and RV capture thresholds simultaneously. The algorithm first acquires templates in the RV-only, LV-only, and Bi-V pacing configurations at steps B1, B2, and B3. After creation of the templates, the system begins decreasing RV and LV pacing amplitudes simultaneously with each pace as indicated by steps B4 and B5, respectively. Similar to the previous algorithm, the RV pace triggers the creation of a test waveform. Cross correlations are then performed between the test waveform and the three templates. If a high correlation exists between the test waveform and the Bi-V template at step B6, both pace amplitudes are assumed to still be above the capture threshold value and the algorithm returns to steps B4 and B5. Otherwise cross-correlations between the test waveform and the RV-only and LV-only templates are performed at step B7. If a high correlation exists between the LV-only template and the test waveform, then the RV pacing amplitude has dropped below the threshold voltage, and the RV capture threshold is found at step B10. Likewise, a high correlation between the test waveform and the RV-only template indicates that the LV pace amplitude has dropped below the threshold voltage, and the LV capture threshold is found at step B8. If a capture threshold is found for a pacing channel at either step B8 or B10, steps B9 and B11 then test whether a capture threshold for the other pacing channel has been found so that the procedure can either end at step B13 or return to step B4 or B5. If the system indicates no correlation between the test waveform and any of the templates, then both pacing channels have dropped below the threshold value. The capture thresholds for both pacing channels are then found so that the pacing thresholds can be adjusted accordingly as indicated by steps B12 and B13.

Figure 3C:
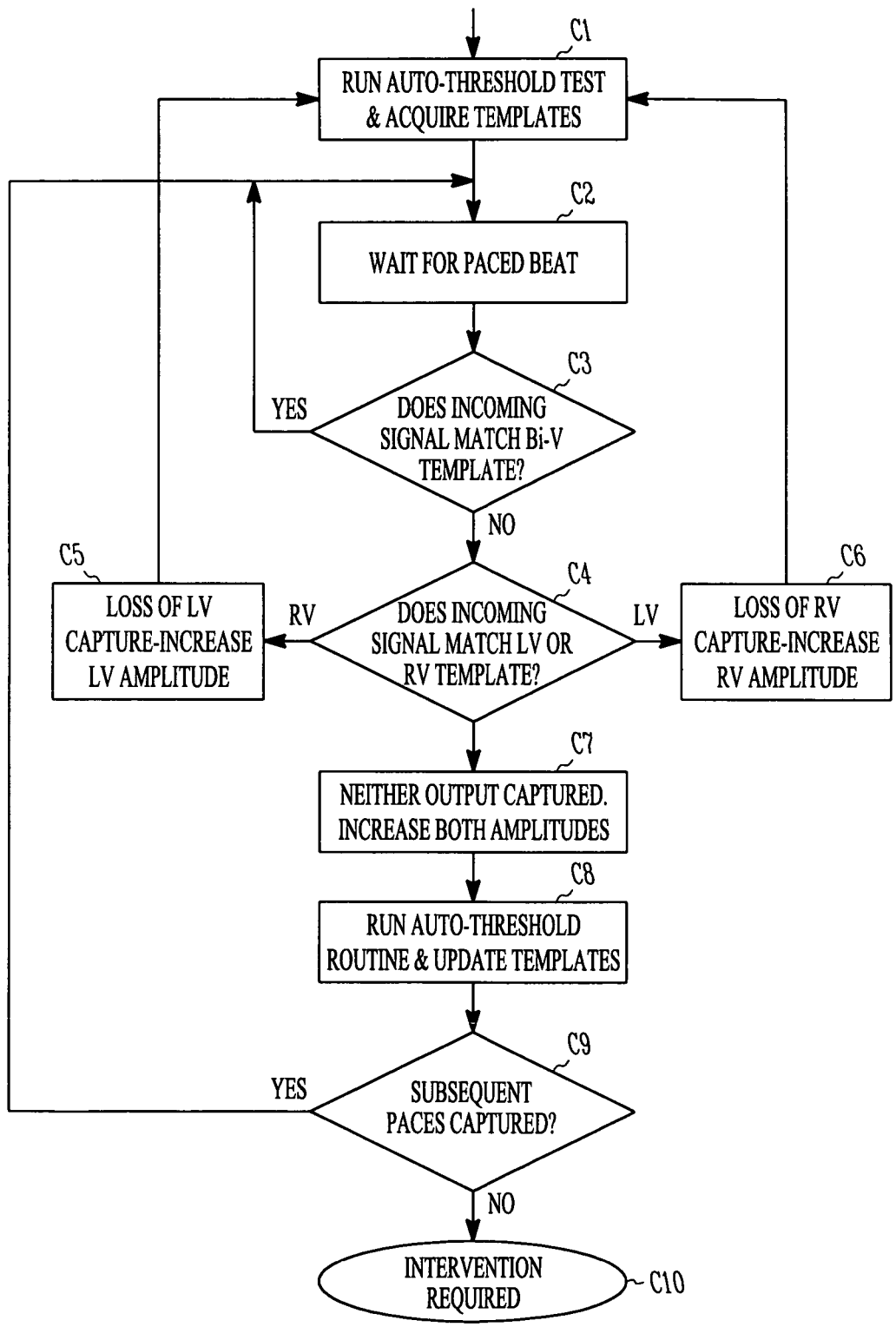
FIGS. 3C and 3D illustrate exemplary embodiments of an auto-capture algorithm.
Figure 3D:
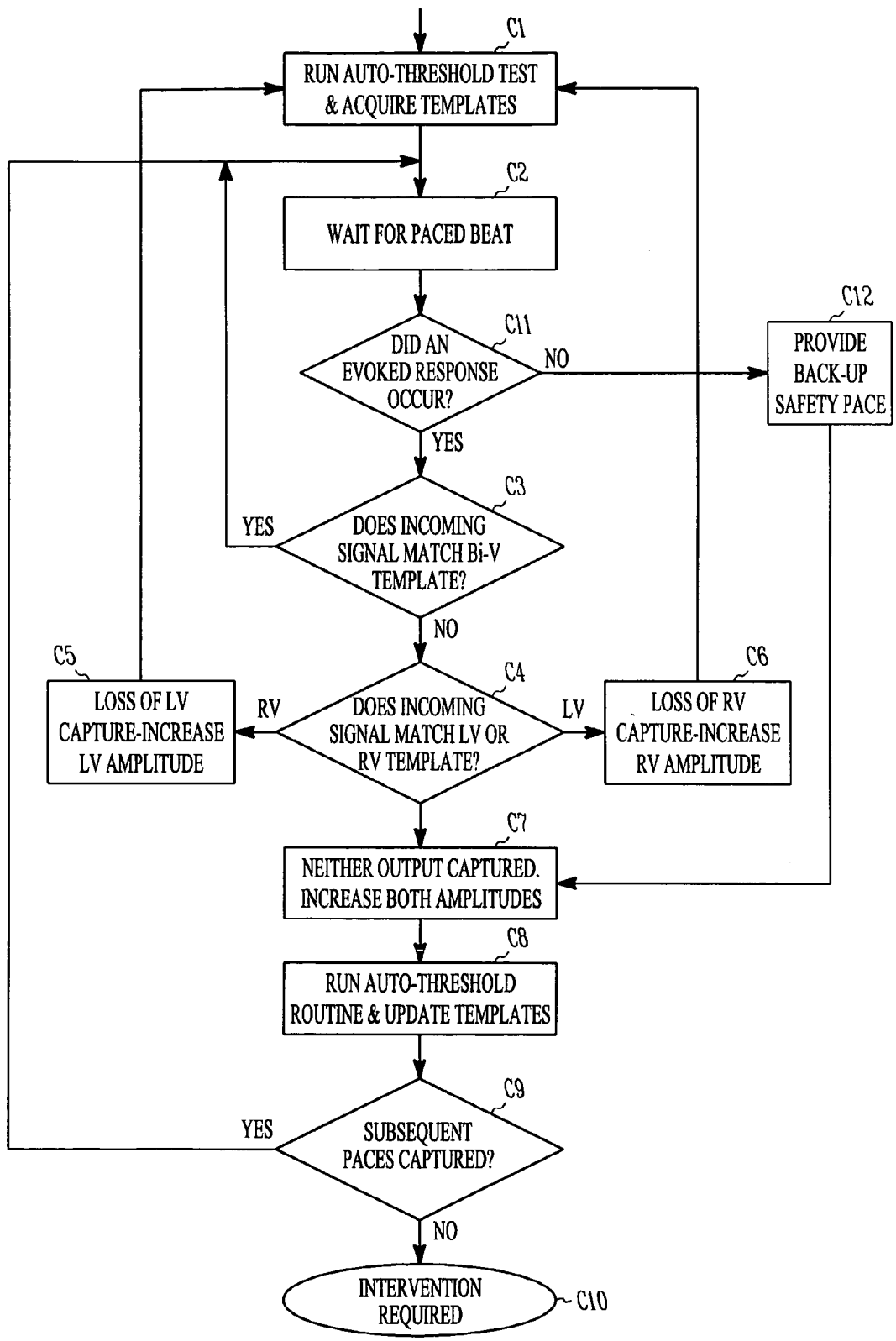

The auto-threshold algorithms illustrated in FIGS. 3A and 3B may be performed by either the pacemaker controller or the processor of an external programmer when it is desired to determine the capture thresholds for the RV and LV pacing channels and set the pacing amplitudes accordingly. As noted above, however, capture verification by cross-correlating template and test waveforms may also be performed on a beat-to-beat basis by the pacemaker controller to provide an ambulatory auto-capture function. FIGS. 3C and 3D illustrate exemplary algorithms for implementing auto-capture in which a capture verification test is performed with each pace.

Referring first to FIG. 3C, the controller performs an auto-threshold algorithm at step C1 in which templates are acquired in the RV-only, LV-only, and Bi-V pacing configurations and capture thresholds are determined for the LV and RV pacing channels so that the pacing pulse amplitudes can be set accordingly. The device then operates normally while the algorithm waits for a paced beat at step C2. At step C3, an incoming signal is used as a test waveform and cross-correlated with the Bi-V template to ascertain if both the RV and LV pacing pulses have achieved capture. If the Bi-V template and test waveforms are highly correlated, capture is assumed, and the algorithm loops back to step C2. If a lack of correlation between the test waveform and the Bi-V template is found, the algorithm separately cross-correlates the test waveform with the LV and RV templates at step C4. If the test waveform matches the RV template, lack of capture in the LV pacing channel is assumed. The LV pacing pulse amplitude is then increased at step C5, and the algorithm returns to step C1 so that updated templates can be acquired and an updated capture threshold determined. Similarly, if the test waveform matches the LV template, the RV pacing pulse amplitude is increased at step C6, and the algorithm returns to step C1. If neither the RV nor the LV paces have achieved capture as indicated by a lack of correlation between the test waveform and the two templates, both the RV and LV pacing amplitudes are increased at step C7. An auto-threshold algorithm is then performed at step C8, with the templates and capture thresholds updated and the pacing pulse amplitudes set accordingly. A capture verification test is performed at step C9 as the device operates with the updated pacing pulse amplitudes. If capture is achieved, the algorithm returns to the capture verification loop of steps C2 and C3. If subsequent paces still fail to achieve capture, it can be assumed that the lack of capture is due to factors other than pacing pulse energy such as the occurrence of fusion events, difficulties in obtaining reference templates, or the occurrence of a malfunction in the pacemaker or lead system. An indication that further intervention is required is then logged in memory at step C10 which can be communicated to a clinician during the next communications session with an external programmer.

The ambulatory auto-capture algorithm presented in FIG. 3C relies on the inherent safety of having multiple ventricular pacing sites in the ventricle. In the event that one chamber loses capture, there is a low probability that the other chamber will simultaneously lose capture. Nonetheless, there is a possibility that the pacemaker could lose capture on both chambers simultaneously. When capture of the ventricles does not occur, it is desirable to provide a back-up safety pace to the right ventricle to immediately provide pacing therapy to prevent the patient from feeling light headed or loosing consciousness. Depending upon the particular implementation, the template cross-correlation algorithms presented here could take greater than 100 ms to accurately identify pacing activity. This is usually too long of a delay to deliver a safety pace. Further, if a fusion event occurs, the device must prevent pacing into a t-wave, so it must again react quickly if a safety pace is to be delivered. FIG. 3D is a flowchart diagram showing an ambulatory auto-capture algorithm that uses a traditional evoked response comparator in addition to template recognition. Steps C1 through C10 in FIG. 3D are identical to those described above with reference to FIG. 3C. After each paced beat, however, the algorithm also tests for capture at step C11 with an evoked response comparator that looks for any evoked response above a specified threshold following a pace. If any evoked response occurs from the ventricles, then some cardiac ventricular activity is assumed to have occurred, and the algorithm proceeds to step C3 to perform the template correlations and determine which chamber or chambers were captured. If no evoked response occurs following a pace, on the other hand, then the algorithm applies a safety pace to the right ventricle at step C12 and then proceeds as if neither pacing pulse captured by going to step C7. In this manner, the patient receives pacing therapy without a noticeable delay.

In the capture verification methods described above, a test depolarization waveform, such as an electrogram or ECG signal, is recorded and compared with one or more template waveforms. In certain implementations, this may involve the processor of the pacemaker or external programmer storing samples of a segment of the test waveform in memory and then performing the cross-correlation operation with corresponding samples of a template waveform. Recording and correlation of the test waveform with a template, however, may also be implemented by passing samples of the incoming electrogram or ECG signal through a finite impulse filter that performs the cross-correlation operation. In that case, the filter may be a matched filter having an impulse response equal to a time-reversed version of a template waveform. The test waveform is thus cross-correlated with a template waveform represented by the filter coefficients of the matched filter. Such a matched filter may be provided for each of the RV-only, LV-only, and BiV template waveforms and may be implemented either in code executed by the controller or as one or more dedicated hardware components.

Capture verification by comparing test and template depolarization waveforms of an evoked response has been described above in the context of multi-site pacing where either one or both of the paired atria or one or both of the paired ventricles are paced with multiple paces during a cardiac cycle. It should also be appreciated that a test depolarization waveform, such as an electrogram from an evoked response sensing channel, can be recorded during delivery of a single pacing pulse and then compared with a template waveform representing single-site capture of the heart by a pacing pulse in order to determine if capture has been achieved by the delivered pacing pulse.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system for determining capture thresholds for a multi-site cardiac pacemaker, comprising:
   a pacemaker having: (a) first and second pacing channels with each such channel comprising an electrode for disposing new a chamber of the heart, a pulse generator for outputting pacing pulses, and a channel interface for adjusting the pacing pulse energy, (b) a controller for controlling the operation of the pulse generators in accordance with a programmed pacing mode such that first and second pacing pulses are delivered from the first and second pacing channels, respectively, to one or both of the paired atria or to one or both of the paired ventricles during a cardiac cycle, and (c) a telemetry interface for communicating with an external programmer;
   an external programmer having a controller for processing data received from the pacemaker, wherein the controller is programmed to:
   generate a dual-channel capture template by recording a depolarization waveform produced when first and second pacing pulses are delivered from the first and second pacing channels at an energy sufficient to achieve capture by each of the first and second pacing pulses,
   generate a first channel capture template by recording a depolarization waveform produced when first pacing pulses are delivered from the first pacing channel at an energy sufficient to achieve capture by the first pacing pulses with no pacing pulses delivered by the second pacing channel,
   generate a second channel capture template by recording a depolarization waveform produced when second pacing pulses are delivered from the second pacing channel at an energy sufficient to achieve capture by the second pacing pulses with no pacing pulses delivered by the first pacing channel,
   record a test depolarization waveform when pacing pulses are delivered from the first and second pacing channels,
   compare the test depolarization waveform to the dual-channel capture template, the first channel capture template, and the second channel capture template,
   determine that both the first and second pacing channels have achieved capture if the test depolarization waveform matches the dual-channel capture template;
   determine that the first pacing channel has failed to achieve capture if the test depolarization waveform does not match the dual-channel capture template but matches the second channel capture template,
   determine that the second pacing channel has failed to achieve capture if the test depolarization waveform does not match the dual-channel capture template but matches the first channel capture template, and
   determine that neither the first nor the second pacing channel has achieved capture if the test depolarization waveform matches neither the dual-channel capture template, the first channel capture template, nor the second channel capture template.

2. The system of claim 1 further comprising an evoked response sensing channel in the pacemaker comprising an electrode and a sense amplifier for sensing an evoked response generated after a pacing pulse and wherein the test waveform is an electrogram from the evoked response sensing channel and transmitted to the external programmer.

3. The system of claim 1 wherein the test waveform is a surface electrocardiogram.

4. The system of claim 1 wherein the controller of the external programmer is programmed to compare the test and template waveforms by performing a time-domain cross-correlation.

5. The system of claim 1 wherein the external programmer controller is further programmed to vary the pulse energy of the pacing pulses in order to determine a capture threshold for a pacing channel.

6. The system of claim 5 wherein the external programmer controller is further programmed to lower the pacing pulse energy of a pacing channel until capture is no longer achieved by that channel in order to determine the capture threshold.

7. The system of claim 6 wherein the external programmer controller is programmed to determine a capture threshold for each of the first and second pacing channels by lowering the pacing energy of each pacing channel separately until the test waveform no longer matches a template waveform representing capture by both of the first and second pacing pulses.

8. The system of claim 6 wherein the external programmer controller is programmed to determine a capture threshold of the first and second pacing channels by:
   lowering the pacing energy of the first pacing channel until the test waveform matches a template waveform representing capture by the second pacing pulse but not by the first pacing pulse; and,
   lowering the pacing energy of the second pacing channel until the test waveform matches a template waveform representing capture by the first pacing pulse but not by the second pacing pulse.

9. The system of claim 6 wherein the external programmer controller is programmed to:

lower the pacing energy of the first and second pacing channels simultaneously until the test waveform no longer matches a template waveform representing capture by both of the first and second pacing pulses;

compare the test waveform to a template waveform representing capture by a pacing pulse delivered only from the first pacing channel and to a template waveform representing capture by a pacing pulse delivered only from the second pacing channel to determine the capture threshold of the pacing channel or channels that failed to capture in the previous step; and, determine the capture threshold of a pacing channel that succeeded in capturing in the previous step by lowering the pacing energy of that channel until the test waveform no longer matches a template waveform representing capture by a pacing pulse delivered individually from that channel.

10. The system of claim 5 wherein the external programmer controller is further programmed to adjust the pacing pulse energy of a pacing channel in accordance with the results of the capture threshold determination.

11. A method for determining capture thresholds for a multi-site cardiac pacemaker, comprising:

delivering first and second pacing pulses through first and second pacing channels, respectively, to either the atria or the ventricles during a cardiac cycle in accordance with a programmed pacing mode;

generating a dual-channel capture template by recording a depolarization waveform produced when first and second pacing pulses are delivered from the first and second pacing channels at an energy sufficient to achieve capture by each of the first and second pacing pulses, generating a first channel capture template by recording a depolarization waveform produced when first pacing pulses are delivered from the first pacing channel at an energy sufficient to achieve capture by the first pacing pulses with no pacing pulses delivered by the second pacing channel, generating a second channel capture template by recording a depolarization waveform produced when second pacing pulses are delivered from the second pacing channel at an energy sufficient to achieve capture by the second pacing pulses with no pacing pulses delivered by the first pacing channel, recording a test depolarization waveform when pacing pulses are delivered from the first and second pacing channels, comparing the test depolarization waveform to the dual-channel capture template, the first channel capture template, and the second channel capture template, determining that both the first and second pacing channels have achieved capture if the test depolarization waveform matches the dual-channel capture template;

determining that the first pacing channel has failed to achieve capture if the test depolarization waveform does not match the dual-channel capture template but matches the second channel capture template, determining that the second pacing channel has failed to achieve capture if the test depolarization waveform does not match the dual-channel capture template but matches the first channel capture template, and;

determining that neither the first nor the second pacing channel has achieved capture if the test depolarization waveform matches neither the dual-channel capture template, the first channel capture template, nor the second channel capture template.

12. The method of claim 11 wherein the comparison between the test and template waveforms is performed with a time-domain cross-correlation.

13. The method of claim 11 wherein the test waveform is a surface electrocardiogram.

14. The method of claim 11 further comprising varying the pulse energy of the pacing pulses in order to determine a capture threshold for a pacing channel.

15. The method of claim 14 further comprising lowering the pacing pulse energy of a pacing channel until capture is no longer achieved by that channel in order to determine the capture threshold.

16. The method of claim 15 further comprising determining a capture threshold for each of the first and second pacing channels by lowering the pacing energy of each pacing channel separately until the test waveform no longer matches a template waveform representing capture by both of the first and second pacing pulses.

17. The method of claim 15 further comprising determining a capture threshold of the first and second pacing channels by:

lowering the pacing energy of the first pacing channel until the test waveform matches a template waveform representing capture by the second pacing pulse but not by the first pacing pulse; and, lowering the pacing energy of the second pacing channel until the test waveform matches a template waveform representing capture by the first pacing pulse but not by the second pacing pulse.

18. The method of claim 15 further comprising adjusting the pacing pulse energy of a pacing channel in accordance with the results of the capture threshold determination.

19. The method of claim 15 further comprising:

lowering the pacing energy of the first and second pacing channels simultaneously until the test waveform no longer matches a template waveform representing capture by both of the first and second pacing pulses;

comparing the test waveform to a template waveform representing capture by a pacing pulse delivered only from the first pacing channel and to a template waveform representing capture by a pacing pulse delivered only from the second pacing channel to determine the capture threshold of the pacing channel or channels that failed to capture in the previous step; and, determining the capture threshold of a pacing channel that succeeded in capturing in the previous step by lowering the pacing energy of that channel until the test waveform no longer matches a template waveform representing capture by a pacing pulse delivered individually from that channel.

* * * * *

UNITED STATES PATENT AND TRADEMARK OFFICE
CERTIFICATE OF CORRECTION

PATENT NO. : 7,177,689 B2
APPLICATION NO. : 10/003718
DATED : February 13, 2007
INVENTOR(S) : Ternes et al.

It is certified that error appears in the above-identified patent and that said Letters Patent is hereby corrected as shown below:

In column 9, line 40, in Claim 1, delete "new" and insert -- near --, therefor.

Signed and Sealed this

First Day of May, 2007

JON W. DUDAS
*Director of the United States Patent and Trademark Office*